United States Patent
Lee et al.

(10) Patent No.: US 10,518,261 B2
(45) Date of Patent: Dec. 31, 2019

(54) SYSTEM CONFIGURED TO DETECT A PATTERN ON A MICROFLUIDIC DEVICE AND DETERMINE THAT THE MICROFLUIDIC DEVICE HAS NOT BEEN NORMALLY LOADED IN A TEST APPARATUS

(71) Applicant: NEXUS DX, INC., San Diego, CA (US)

(72) Inventors: Jung Tae Lee, Jeonju-si (KR); Chung Ung Kim, Yongin-si (KR); Young Goun Lee, Seoul (KR); Jin Beom Hong, Seoul (KR)

(73) Assignee: NEXUS DX, INC., San Diego, CA (US)

( * ) Notice: Subject to any disclaimer, the term of this patent is extended or adjusted under 35 U.S.C. 154(b) by 1496 days.

(21) Appl. No.: 13/930,772

(22) Filed: Jun. 28, 2013

(65) Prior Publication Data

US 2014/0363895 A1    Dec. 11, 2014

(30) Foreign Application Priority Data

Jun. 5, 2013    (KR) .......................... 10-2013-0064915

(51) Int. Cl.
*G01N 35/00* (2006.01)
*B01L 3/00* (2006.01)
(Continued)

(52) U.S. Cl.
CPC .......... *B01L 3/5027* (2013.01); *B04B 5/0407* (2013.01); *B04B 13/00* (2013.01);
(Continued)

(58) Field of Classification Search
None
See application file for complete search history.

(56) References Cited

U.S. PATENT DOCUMENTS

| | | | | |
|---|---|---|---|---|
| 4,140,397 A | * | 2/1979 | Gara | G01B 11/303 250/559.44 |
| 2009/0253130 A1 | * | 10/2009 | Yoo | B01F 13/0059 435/6.11 |

(Continued)

*Primary Examiner* — Christopher Adam Hixson
*Assistant Examiner* — Michelle Adams
(74) *Attorney, Agent, or Firm* — Knobbe, Martens, Olson & Bear, LLP

(57) ABSTRACT

A test apparatus is provided for rapidly detecting abnormal loading of a microfluidic device, and unloading the abnormally-loaded microfluidic device, thereby preventing contamination of the test apparatus by a sample and degradation in reliability of test results. A test system including the test apparatus and a control method for the test apparatus are also provided. The test apparatus includes an optical sensor to photograph an image at a position corresponding to the microfluidic device, and a controller to detect a pattern formed on a surface of the microfluidic device based on the photographed image to determine whether characteristics of the detected pattern are identical to characteristics of a pre-stored pattern, and to determine whether the microfluidic device has not been normally loaded, when the characteristics of the detected pattern are different from the characteristics of the pre-stored pattern.

33 Claims, 20 Drawing Sheets

NORMAL LOADING

LOADING UPSIDE DOWN

(51) Int. Cl.
  *B04B 5/04*    (2006.01)
  *B04B 13/00*   (2006.01)
  *G01N 21/07*   (2006.01)
  *G01N 21/00*   (2006.01)
  *G01N 35/04*   (2006.01)

(52) U.S. Cl.
  CPC ........... *B04B 13/003* (2013.01); *G01N 21/07* (2013.01); *G01N 35/00069* (2013.01); *B01L 2200/025* (2013.01); *B01L 2200/143* (2013.01); *B01L 2300/0803* (2013.01); *B01L 2400/0406* (2013.01); *B01L 2400/0409* (2013.01); *G01N 2035/00158* (2013.01); *G01N 2035/0494* (2013.01)

(56) References Cited

U.S. PATENT DOCUMENTS

| | | | | |
|---|---|---|---|---|
| 2009/0308470 | A1* | 12/2009 | Bergstrom | B01L 3/5027 137/624.11 |
| 2010/0093105 | A1* | 4/2010 | Lee | B07C 5/3416 436/171 |
| 2011/0253224 | A1* | 10/2011 | Linder | B01L 3/5027 137/2 |
| 2011/0306506 | A1* | 12/2011 | Demierre | B01L 3/502761 506/7 |

* cited by examiner

SYSTEM CONFIGURED TO DETECT A PATTERN ON A MICROFLUIDIC DEVICE AND DETERMINE THAT THE MICROFLUIDIC DEVICE HAS NOT BEEN NORMALLY LOADED IN A TEST APPARATUS

CROSS-REFERENCE TO RELATED APPLICATION

This application claims priority from Korean Patent Application No. 10-2013-64915, filed on Jun. 5, 2013 in the Korean Intellectual Property Office, the disclosure of which is incorporated herein by reference.

BACKGROUND

1. Field

Apparatuses and methods consistent with exemplary embodiments relate to a microfluidic device and a test apparatus usable in testing a sample, a test system having the same, and a control method for the test apparatus.

2. Description of the Related Art

Recently, technologies associated with a test apparatus employing a microfluidic structure in order to analyze a small amount of blood, urine, etc., for diagnosis of a particular disease or determination as to presence of a particular substance, have advanced.

For analysis of a sample, the sample is injected into a microfluidic device formed with a microfluidic structure, and the microfluidic device is loaded in a test apparatus and is then rotated in accordance with a predetermined sequence. As the microfluidic device rotates, the sample is moved and, as such, a reaction required in analysis occurs with the sample.

In a procedure of loading the microfluidic device in the test apparatus, the tester may load the microfluidic device upside down. When the microfluidic device is loaded in the test apparatus upside down, the sample injected into the microfluidic device may be discharged into the interior of the test apparatus. Thus, when an image sensor configured to photograph results of testing is positioned beneath the microfluidic device, it may become contaminated by the discharged sample.

When the interior of the test apparatus or the image sensor is contaminated, erroneous test results may be obtained. As a result, there may be degradation in accuracy of test results. Furthermore, when the microfluidic device rotates upside down, the sample may be sprayed throughout the interior of the test apparatus. As a result, reliability of the test apparatus may be considerably degraded, and the test apparatus may malfunction.

SUMMARY

Exemplary embodiments provide a microfluidic device, a test apparatus, a test system having the same, and a control method for the test apparatus, which are capable of rapidly detecting abnormal loading of the microfluidic device in the test apparatus, and unloading the abnormally-loaded microfluidic device, thereby preventing contamination of the test apparatus by a sample and degradation in reliability of test results.

In accordance with an aspect of an exemplary embodiment, there is provided a test apparatus for testing a sample received in a microfluidic device, the test apparatus including an optical sensor configured to photograph an image at a position corresponding to the microfluidic device, and a controller configured to detect a pattern formed on a surface of the microfluidic device based on the photographed image, and to determine that the microfluidic device has not been normally loaded based on characteristics of the detected pattern.

The controller may be configured to determine whether characteristics of the detected pattern are identical to characteristics of a pre-stored pattern, and to determine whether the microfluidic device has been normally loaded based on a result of the determination of whether the characteristics of the detected pattern are identical to the characteristics of the pre-stored pattern.

The controller may be configured to determine that the microfluidic device has not been normally loaded when it is determined that the characteristics of the detected pattern are different from the characteristics of the pre-stored pattern.

The pre-stored pattern may be a pattern corresponding to normal loading of the microfluidic device.

The controller may be configured to determine whether the microfluidic device has been loaded upside down.

The controller may be configured to pre-store a direction of pattern corresponding to normal loading of the microfluidic device, to determine whether a vertical or lateral direction of the detected pattern is opposite to the pre-stored pattern direction, and to determine that the microfluidic device has been loaded upside down upon determining that the vertical or lateral direction of the detected pattern is opposite to the pre-stored pattern direction.

The test apparatus may further include a tray insertable into and ejectable from an interior of the test apparatus. The tray may carry the microfluidic device.

The controller may be further configured to control the optical sensor to photograph an image at a position corresponding to the microfluidic device when the tray is inserted into the test apparatus.

The controller may be configured to control the tray to be ejected from the test apparatus, upon determining that the microfluidic device has not been normally loaded.

The optical sensor may be movable in a radial direction of the microfluidic device.

The position corresponding to the microfluidic device may be a position that corresponds to a pattern region including the pattern.

The controller may be configured to position the optical sensor at an initial position corresponding to the microfluidic device.

The controller may be configured to compensate for a difference between a brightness value of a pattern exhibited in the photographed image and a reference brightness value applied for detection of the pattern.

The pattern formed on the microfluidic device may include a plurality of pattern elements. The controller may be configured to detect a reference element from among the plurality of pattern elements in the photographed image, and to adjust a threshold value corresponding to the reference brightness value based on a representative brightness value of the detected reference pattern element.

The test apparatus may further include a storage unit configured to store one or more of the photographed image and results of determining that the microfluidic device has not been normally loaded.

The test apparatus may further include a light emitter mounted at a position facing the optical sensor or in parallel with the optical sensor.

In accordance with an aspect of another exemplary embodiment, there is provided a microfluidic device including a platform including a pattern having a vertically or laterally asymmetrical shape, and a microfluidic structure including an inlet configured to inject a sample, a plurality of chambers configured to receive the sample or a substance to be used for a test, and at least one channel configured to connect the plurality of chambers.

The pattern may be printed on a surface of the microfluidic device, may be printed on a label attached to the surface of the microfluidic device, or may be engraved on the surface of the microfluidic device.

The pattern may be repeatedly arranged in a circumferential direction of the microfluidic device.

In accordance with another exemplary aspect, a test system includes the test apparatus, and a microfluidic device having disposed thereon a pattern having a vertically or laterally asymmetrical shape.

In accordance with an aspect of another exemplary embodiment, there is provided a control method for a test apparatus for determining normal loading of a microfluidic device, the control method including photographing an image at a position corresponding to a microfluidic device when a tray carrying the microfluidic device is inserted into the test apparatus, detecting a pattern formed on the microfluidic device from the photographed image, and determining whether the microfluidic device has been normally loaded based on characteristics of the detected pattern.

The determining whether the microfluidic device has been normally loaded may include determining whether characteristics of the detected pattern are identical to characteristics of a pre-stored pattern, and determining whether the microfluidic device has been normally loaded based on a result of the determination of whether the characteristics of the detected pattern are identical to the characteristics of the pre-stored pattern.

It may be determined that the microfluidic device has not been normally loaded when it is determined that the characteristics of the detected pattern are different from the characteristics of the pre-stored pattern.

The predetermined pattern may be a pattern corresponding to normal loading of the microfluidic device.

The determining that the characteristics of the detected pattern are different from the characteristics of the predetermined pattern may include determining whether the microfluidic device has been loaded upside down.

The determining whether the characteristics of the detected pattern are identical to the characteristics of the predetermined pattern may include pre-storing a direction of the pattern corresponding to normal loading of the microfluidic device, determining whether a vertical or lateral direction of the detected pattern is opposite to the pre-stored pattern direction, and determining that the microfluidic device has been loaded upside down, upon determining that the vertical or lateral direction of the detected pattern is opposite to the pre-stored pattern direction.

The control method may further include ejecting the tray upon determining that the microfluidic device has not been normally loaded.

The position corresponding to the microfluidic device may be a position corresponds to a pattern region including the pattern.

The control method may further include moving the optical sensor to the position corresponding to the microfluidic device before photographing the image.

The control method may further include compensating for a difference between a brightness value of a pattern exhibited in the photographed image and a reference brightness value applied for detection of the pattern.

The compensating may include detecting a reference pattern element included in the pattern from the photographed image, and adjusting a threshold value corresponding to the reference brightness value based on a representative brightness value of the detected reference pattern element.

The control method may further include storing one or more of the photographed image and results of determining that the microfluidic device has not been normally loaded, upon determining that the microfluidic device has not been normally loaded.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Hereinafter, exemplary embodiments will be described with reference to the accompanying drawings.

Figure 1A:
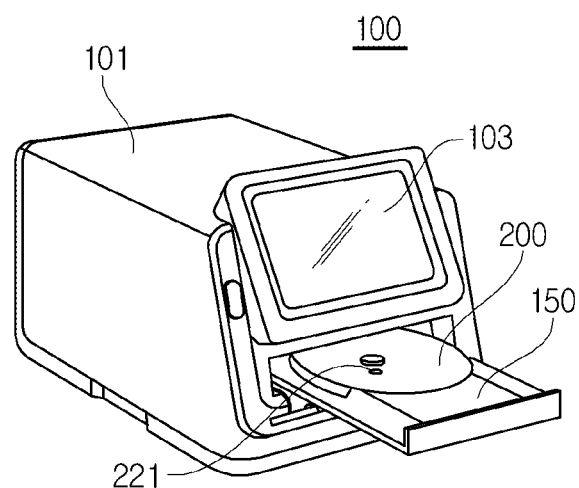
FIGS. 1A and 1B are perspective views illustrating an appearance of a test apparatus according to an exemplary embodiment.
Figure 1B:
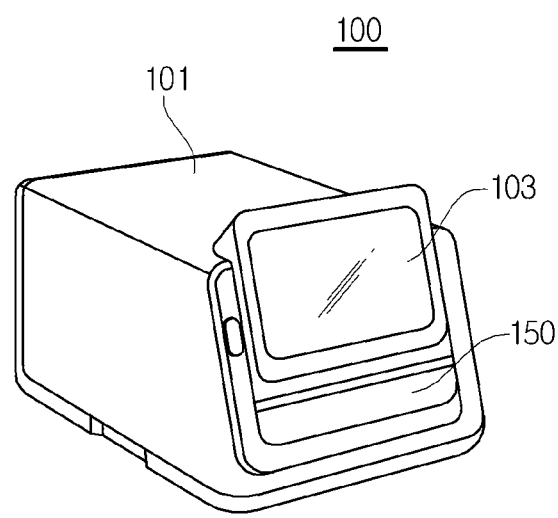

FIGS. 1A and 1B are perspective views illustrating an appearance of a test apparatus according to an exemplary embodiment.

Referring to FIGS. 1A and 1B, the test apparatus 100 includes a housing 101, and a tray 150 slidably mounted in the housing 150 such that the tray 150 is ejectable from the housing 101. A microfluidic device 200 is loadable in the tray 150. For testing of a sample, the user injects the sample into the microfluidic device 200 through an inlet 221 provided at a surface of the microfluidic device 200, and loads the sample-injected microfluidic device 200 onto the tray 150. After the microfluidic device 200 is loaded onto the tray 150, the tray 150 is inserted into the test apparatus 100. Thus, the microfluidic device 200 is loaded in the test apparatus 100.

The test apparatus 100 may also include a display 103 to display the current state of the test apparatus 100 and/or test results, and/or to display a menu associated with control of the test apparatus 100 in order to allow the user to input a control command. To this end, the test apparatus 100 may include a separate input unit. Alternatively, the display 103 may be a touch screen or a touch panel in order to function as the input unit.

For example, when the user inputs a control command associated with ejection of the tray 150 through the input unit, the tray 150 is ejected, as shown in FIG. 1A. On the other hand, when the user inputs a control command associated with insertion of the tray 150 or pushes the tray 150, the tray 150 is retracted, as shown in FIG. 1B, and, as such, the microfluidic device 200 is loaded in the test apparatus 100.

The microfluidic device 200 includes top and bottom sides that are distinguished from each other. When the microfluidic device 200 is loaded right side up in the test apparatus 100 (i.e., when the inlet 221 is facing upward), the loading is considered to be normal.

However, abnormal loading of the microfluidic device 200 may occur. For example, the microfluidic device 200 may be loaded upside down (i.e., when the inlet 221 is facing downward). When the microfluidic device 200 is loaded upside down, the sample injected into the microfluidic device 200 may leak out of the microfluidic device 200. The leaked sample may then contaminate the interior of the test apparatus 100, which includes sensitive elements. Such contamination may cause erroneous test results or failure of the test apparatus.

Furthermore, when the microfluidic device 200 rotates upside down, the sample may spray throughout the interior of the test apparatus. As a result, reliability of the test apparatus may be considerably degraded.

To this end, the test apparatus 100 rapidly determines whether the microfluidic device 200 has been normally loaded. When the microfluidic device 200 is abnormally loaded, the test apparatus 100 immediately unloads the microfluidic device 200, to minimize possibility of contamination of the test apparatus 100.

Figure 2:
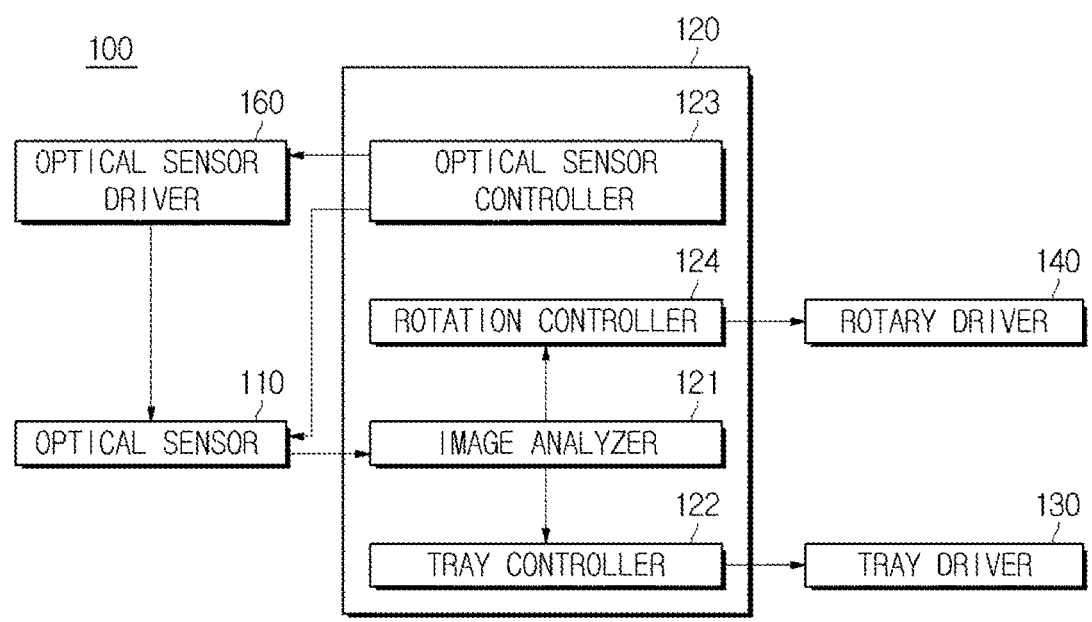
FIG. 2 is a block diagram illustrating a control configuration of the test apparatus according to an exemplary embodiment.

FIG. 2 is a block diagram illustrating a control configuration of the test apparatus according to an exemplary embodiment.

Referring to FIG. 2, the test apparatus 100 includes an optical sensor 110 configured to photograph an image at a position corresponding to the microfluidic device 200, and a controller 120 configured to analyze the photographed image, to detect a pattern formed on a surface of the microfluidic device 200 based on results of the analysis, and to determine whether the microfluidic device 200 has been normally loaded based on the detected pattern.

As will be described later, a pattern is formed on a surface of the microfluidic device 200. The above-described position which corresponds to the microfluidic device 200 is a position corresponding to a pattern region, namely, a position where the pattern region may be photographed or a position facing the pattern region. The pattern region is a predetermined region including the pattern formed on the surface of the microfluidic device 200. Accordingly, the image photographed by the optical sensor 110 may be a pattern region image. Information as to the shape and/or optical characteristics of the pattern is pre-stored in the test apparatus 100.

Meanwhile, there may be an occasion when the tray 150 is in the closed position and there is no microfluidic device 200 loaded in the test apparatus 100. In another case, even when a microfluidic device 200 is loaded in the test apparatus 100, the loaded microfluidic device 200 may be a microfluidic device having no pattern. Even in such cases, the optical sensor 110 photographs an image. Therefore, it should be understood that the pattern region image includes all images photographed by the optical sensor 110 at a position corresponding to the pattern region of the microfluidic device 200, irrespective of whether or not the pattern region is actually photographed.

The optical sensor may include an image sensor. The image sensor may be a charge coupled device (CCD) image sensor or a complementary metal oxide semiconductor (CMOS) image sensor.

The test apparatus 100 may further include a tray driver 130 configured to move the tray 150, a rotary driver 140 configured to rotate the microfluidic device 200, and an optical sensor driver 160 configured to move the optical sensor 110. Operation of the drivers may be controlled by the controller 120.

The controller 120 includes an image analyzer 121 configured to analyze a pattern region image photographed by the optical sensor 110, and to determine whether the microfluidic device 200 has been normally loaded based on results of the analysis, and an optical sensor controller 122 configured to control the optical sensor 110 and optical sensor driver 160. The controller 120 also includes a tray controller 123 configured to control the tray 150 to be ejected upon determining that the microfluidic device 200 has not been normally loaded, and a rotation controller 124 configured to transmit a control signal to the rotary driver 140 in accordance with a predetermined test sequence upon determining that the microfluidic device 200 has been normally loaded, so as to control an operation such as movement of a fluid and/or centrifugal separation of the fluid.

When the microfluidic device 200 has not been normally loaded, in particular, when the microfluidic device 200 has been loaded upside down, it is important to immediately unload the microfluidic device 200 before rotation of the microfluidic device 200 occurs, in order to minimize contamination of the test apparatus 100. To this end, the optical sensor controller 122 controls the optical sensor 110 to photograph a pattern region image immediately after the tray 150 is inserted.

The photographed pattern region image is then transmitted to the image analyzer 121. Then, the image analyzer 121 detects a pattern from the pattern region image. Based on the detected pattern, the image analyzer 121 determines whether the microfluidic device 200 has been normally loaded.

When the image analyzer 121 determines that the microfluidic device 200 has not been normally loaded, the tray controller 123 transmits an ejection signal to the tray driver 130, to eject the tray 150. On the other hand, when the image analyzer 121 determines that the microfluidic device 200 has been normally loaded, the rotation controller 124 transmits a rotation signal to the rotary driver 140, to rotate the microfluidic device 200. Thus, a test is begun.

Situations in which the image analyzer 121 determines that the microfluidic device 200 has not been normally loaded may include when there is no microfluidic device 200 loaded in the test apparatus 100, and when although the microfluidic device 200 has been normally loaded, it does not have a pattern corresponding to the stored pattern information. In such cases, the tray controller 123 transmits an ejection signal to the tray driver 130, thereby ejecting the tray 150.

As described above, the test apparatus 100 is configured to determine whether the microfluidic device 200 has not been normally loaded by detecting the pattern formed on a surface of the microfluidic device 200. Hereinafter, the microfluidic device 200 will be described before description of concrete operations of the test apparatus 100.

Figure 3A:
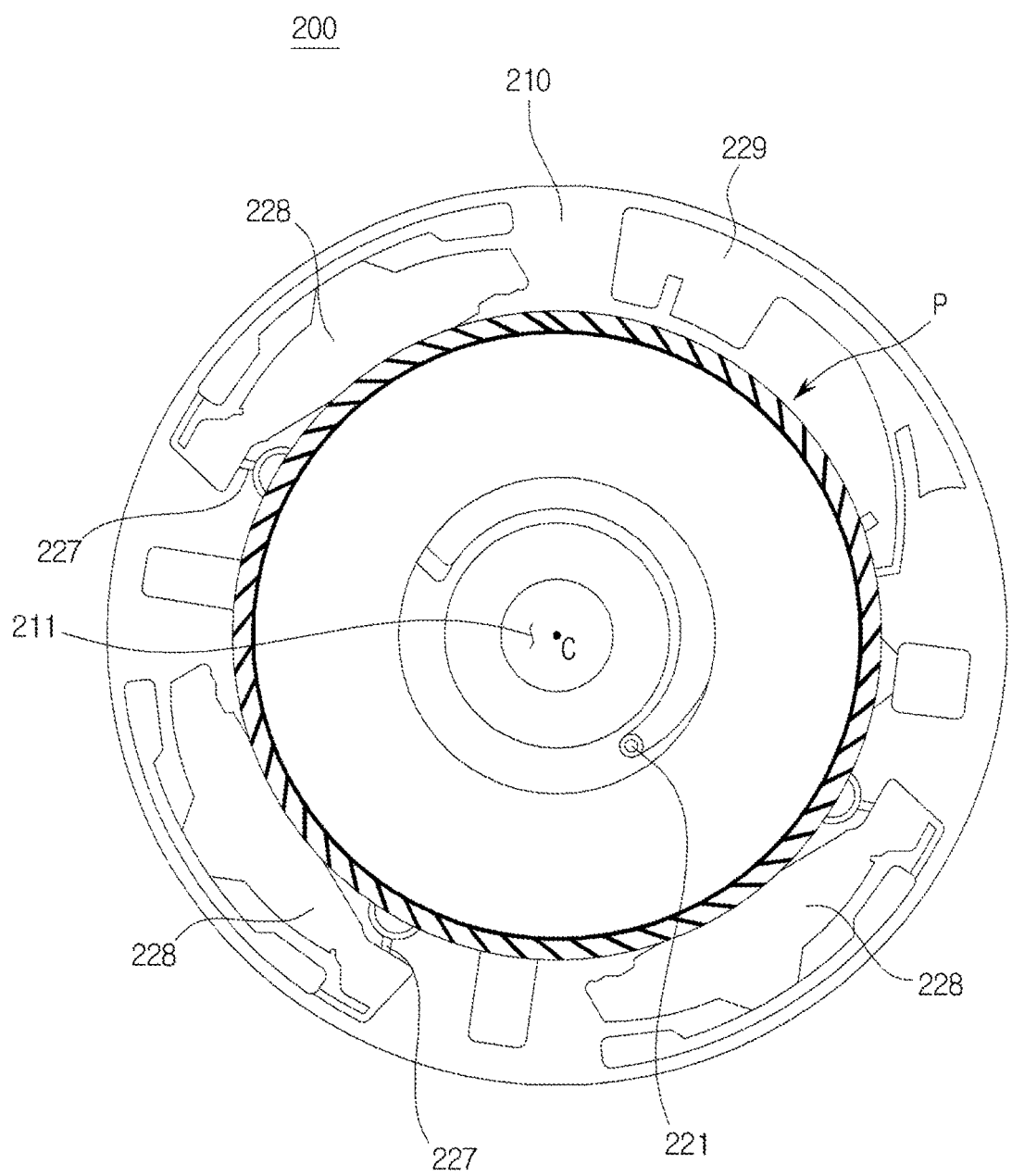
FIGS. 3A and 3B are plan views of a microfluidic device according to an exemplary embodiment.
Figure 3B:
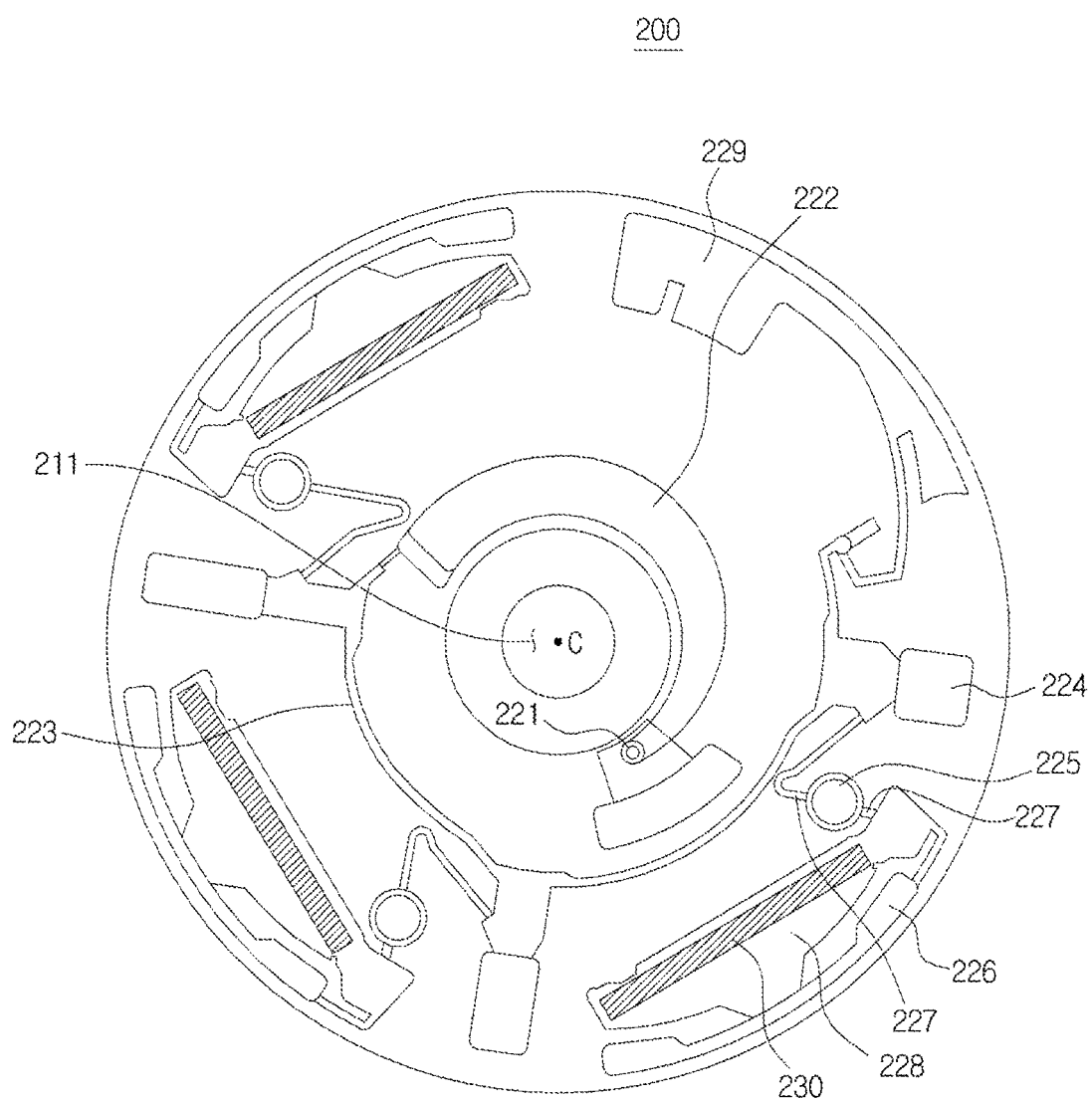

FIGS. 3A and 3B are plan views of the microfluidic device according to the illustrated exemplary embodiment. In the illustrated embodiment, it is assumed that the surface of the microfluidic device 200, at which the inlet 221 is formed, is a plan surface or a top surface.

Referring to FIG. 3A, the microfluidic device 200 includes a platform 210 having a rotation center C and a through hole 211, and a microfluidic structure formed within the platform 210.

In the illustrated exemplary embodiment, the microfluidic structure does not refer to a structure having a particular shape, but inclusively means structures such as chambers 228 and 229 and channels 227. The microfluidic structure may therefore be used to perform different functions in accordance with the characteristics of different arrangements thereof and/or different kinds of materials received therein.

The platform 210 may be made of any of various materials having easy moldability while exhibiting biological inactivity at a surface thereof, for example, a plastic material such as an acrylate (polymethyl methacrylate (PMMA)), polydimethylsiloxane (PDMS), polycarbonate (PC), polypropylene, polyvinyl alcohol, or polyethylene, glass, mica, silica, or silicon wafer. However, these materials are only illustrative examples of materials usable as the material of the platform 100, and the exemplary embodiments are not limited thereto. Thus, any material may be used as the material of the platform 210, so long as such material exhibits chemical and biological stability, optical transparency, and mechanical workability.

The platform 210 may include a plurality of vertically-layered plates. It may be possible to provide within the platform 210 a space to receive a fluid and a passage to allow the fluid to move by forming an engraved structure corresponding to a microfluidic structure, such as a chamber or a channel, at the contact surfaces of two plates, and then bonding the plates to each other. Bonding of the facing plates may be accomplished using any of various methods such as bonding with a double-sided adhesive tape, ultrasonic fusing, and laser welding.

Although the platform 210 employed in the microfluidic device 200 is of a disc type in the exemplary embodiment of FIG. 3A, it may have a sector shape or a polygonal shape.

As shown in FIG. 3A, the pattern which is designated by reference character "P" may be formed on a surface of the platform 210. In the illustrated embodiment, the pattern P is printed on a portion of a label attached to a surface of the platform 210. However, the pattern P is not limited to the illustrated embodiment, and may be directly printed or carved onto the surface of the platform 210.

In the illustrated exemplary embodiment, the pattern P is formed on an upper surface of the platform 210. However, the pattern P is not limited to the illustrated embodiment, and may be formed on a lower surface of the platform 210. It should be understood that because the platform 210 constitutes a body of the microfluidic device 200, formation of the pattern P on the platform 210 or on a surface of the platform 210 means formation of the pattern P on the microfluidic device 200 or on a surface of the microfluidic device 200.

The pattern P may have a shape such that, when the pattern P is reversed, the reversed pattern P is vertically or laterally opposite to the normal pattern P. That is, the pattern P may have a vertically or laterally asymmetrical shape. Thus, when the microfluidic device 200 is loaded in the test apparatus 100 upside down, the pattern P is photographed upside down. The image analyzer 121 then determines that the pattern P is upside down, through analysis of the pattern region image. Based on results of such a determination, it may be possible to recognize abnormal loading of the microfluidic device 200.

The pattern P may include a plurality of pattern elements. For example, the pattern P may have a comb shape including a plurality of bars inclined in a predetermined direction, as shown in FIG. 3A. When the comb shape according to the exemplary embodiment of FIG. 3A is reversed, the reversed comb shape is opposite to the normal comb shape. Accordingly, the image analyzer 121 may determine, based on the direction of the teeth of the comb, whether the microfluidic device 200 has been abnormally loaded. This will be described in detail later.

Meanwhile, the microfluidic structure may have various shapes in accordance with the purpose of the test, the kind of the test, and the test method. For example, the microfluidic structure illustrated in FIG. 3B may be employed to detect whether a particular substance is present in blood. Hereinafter, microfluidic structures included in the microfluidic device 200 in accordance with exemplary embodiments will be described in brief.

As described above, the platform 210 is rotated by the rotary driver 140. In accordance with centrifugal force generated during rotation of the platform 210, a material, for example, a fluid, received in the microfluidic structure may be moved. In this regard, the inlet 221 and a reservoir 222 connected to the inlet 221 may be provided at a position nearest to the rotation center C of the platform 210. The reservoir 222 is connected to a distribution channel 223 and, as such, the fluid, namely, a sample, is supplied to three centrifugal separation chambers 224.

The sample received in the microfluidic device 200, that is, the sample to be tested by the test apparatus 100, may be a fluid sample such as blood, urine, lymph, or tissue fluid. Of course, the sample is not limited to the above-described fluidic sample, and a sample other than a fluid may be tested by the test apparatus 100.

Each centrifugal separation chamber 224 is connected to a reaction chamber 225 and, as such, a centrifugally separated sample, for example, supernatant of blood, is moved to the reaction chamber 225. A marker may be pre-loaded into the reaction chamber 225 to generate a combination reaction with a target substance of the sample.

The reaction chamber 225 may be connected to a detection chamber 228 and, as such, a reaction product may then be moved to the detection chamber 228. In the detection chamber 228, an indicator paper 230 utilizing chromatography may be provided. Depending on whether a target substance is present in the reaction product, the color of the indicator paper 230 may change. As the optical sensor 110 photographs the detection chamber 228, and thereafter analyzes the photographed image, it may be possible to determine whether a target substance is present in the reaction product.

Of course, the structure of the microfluidic device 200 illustrated in FIGS. 3A and 3B is only illustrative.

Hereinafter, concrete operations of the test apparatus 100 will be described.

Figure 4:
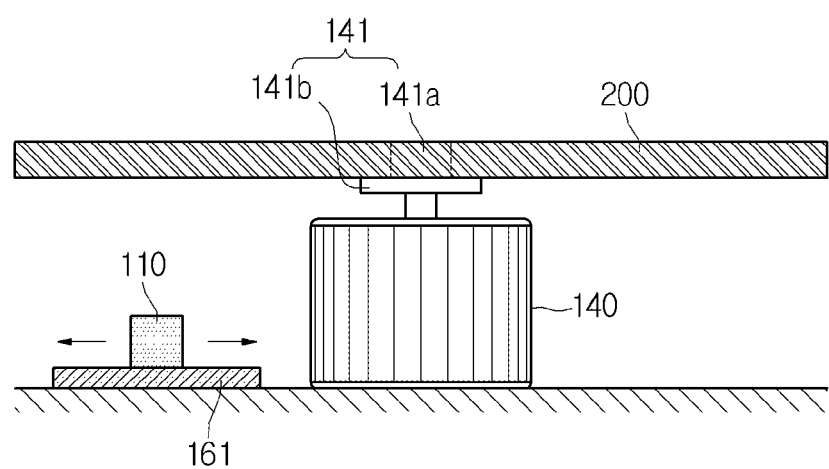
FIG. 4 is a side view illustrating an inner configuration of the test apparatus according to an exemplary embodiment.

FIG. 4 is a side view illustrating an inner configuration of the test apparatus 100 according to an exemplary embodiment. However, in FIG. 4, only a portion of the inner configuration of the test apparatus 100 which is required to be described is illustrated.

Referring to FIG. 4, when the microfluidic device 200 is loaded in the test apparatus 100, a rotation shaft 141a of a turntable 141b is inserted into the through hole 211 provided at the rotation center C of the microfluidic device 200. As a test begins, the turntable 141b rotates the microfluidic device 200 while supporting the microfluidic device 200. Rotational force is supplied from the rotary driver 140. The rotary driver 140 may include a motor and a drive. The drive may drive the motor in accordance with a control signal transmitted from the rotary controller 124.

The optical sensor 110 photographs an image of a pattern region at a position corresponding to the microfluidic device 200. The optical sensor may move along guide rails 161 arranged in a radial direction of the microfluidic device 200. When the microfluidic device 200 is loaded, the optical sensor 110 photographs an image of the pattern region, and then transmits the photographed pattern region image. After a test begins, the optical sensor 110 moves to a position corresponding to a detection region in accordance with a predetermined test sequence, to photograph the detection region.

The optical sensor 110 may be moved by the optical sensor driver 160. The optical sensor driver 160 may include a motor and a drive. The motor may be a linear motor. The drive drives the motor in accordance with a control signal transmitted from the optical sensor driver 123, to supply power for linear movement to the optical sensor 110.

The initial position of the optical sensor 110 corresponds to the position of the microfluidic device 200. The optical sensor controller 123 may move the optical sensor 110 to the initial position before the tray 150 is inserted. The initial position of the optical sensor 110 may be determined in a design stage, and may be calibrated in a product use stage.

Meanwhile, when the optical sensor 110 is disposed beneath the microfluidic device 200, it may be contaminated by the microfluidic device 200 if the microfluidic device 200 is loaded upside down. Accordingly, the initial position of the optical sensor 110 should not face the inlet 221 while corresponding to the pattern region. To this end, the pattern P may be formed at a position spaced away from the inlet 221 in a radial direction relative to the microfluidic device 200.

Although the optical sensor 110 is illustrated as being disposed beneath the microfluidic device 200 in the exemplary embodiment of FIG. 4, various embodiments are not limited thereto. Thus, the optical sensor 110 may be disposed above the microfluidic device 200.

Hereinafter, operation of determining whether the microfluidic device 200 has been normally loaded through analysis of the pattern region image will be described in detail.

Figure 5:
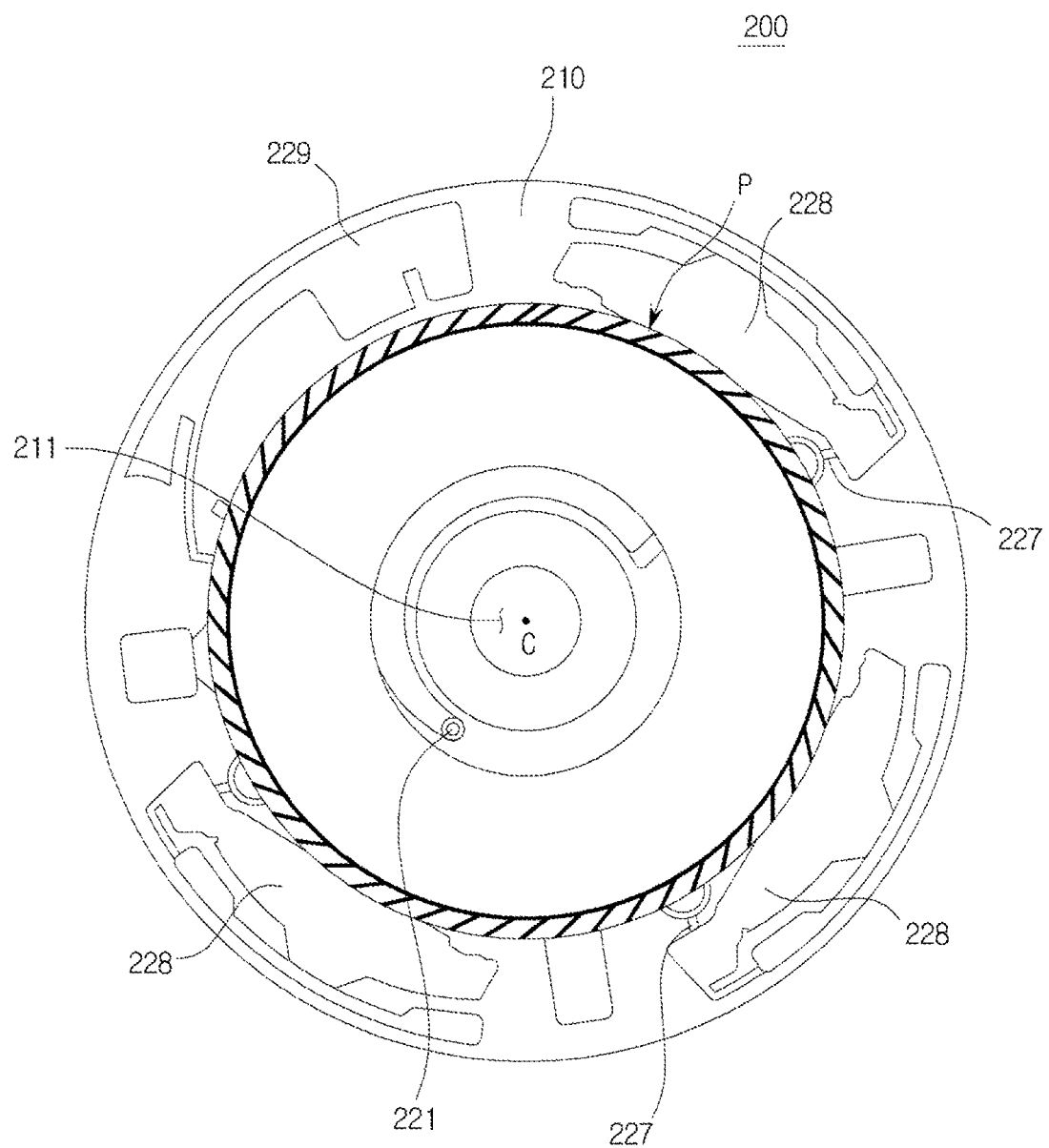
FIG. 5 is a bottom view of a configuration of the microfluidic device according to an exemplary embodiment.
Figure 6:
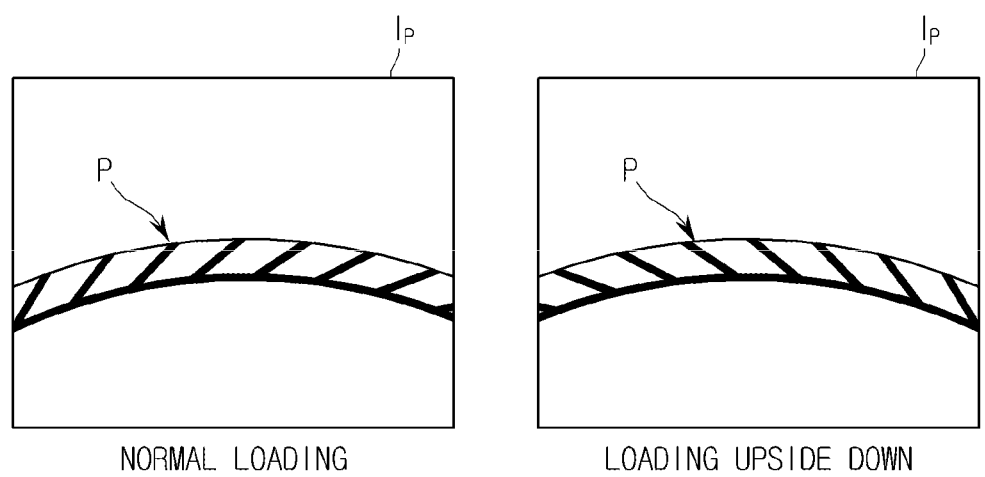
FIG. 6 is a view illustrating a pattern region image when the microfluidic device is normally loaded and a pattern region image when the microfluidic device is loaded upside down.

FIG. 5 is a bottom view of a configuration of the microfluidic device 200 according to an exemplary embodiment. FIG. 6 is a view illustrating a pattern region image when the microfluidic device is normally loaded and a pattern region image when the microfluidic device is loaded upside down.

The microfluidic device 200 illustrated in FIG. 5 is identical to the microfluidic device 200 illustrated in FIG. 2. Since the platform 210 has optical transparency, as described above, the pattern formed on the upper surface of the microfluidic device 200 may be photographed at a bottom side of the microfluidic device 200. As illustrated in FIG. 5, the pattern viewed at the bottom side of the microfluidic device 200 is laterally opposite to the pattern illustrated in FIG. 2.

Assuming that the optical sensor 110 is disposed beneath the microfluidic device 200, the optical sensor 110 photographs the lower surface of the microfluidic device 200 illustrated in FIG. 5 when the microfluidic device 200 is normally loaded.

Accordingly, when the microfluidic device 200 is normally loaded, the comb tooth pattern of a pattern region image Ip photographed by the optical sensor 110 is inclined to the right, as shown in the left panel of FIG. 6. On the other hand, when the microfluidic device 200 is loaded upside down, the comb tooth pattern of a pattern region image Ip photographed by the optical sensor 110 is inclined to the left, as shown in the right panel of FIG. 6.

The image analyzer 121 detects the pattern P from the pattern region image, and determines whether the characteristics of the detected pattern are identical to the characteristics of the stored pattern, namely, the characteristics of the pattern exhibited upon normal loading. Upon determining that the characteristics of the detected pattern are different from the characteristics of the stored pattern, the image analyzer 121 determines that the microfluidic device 200 has not been normally loaded. On the other hand, when the characteristics of the detected pattern are identical to the characteristics of the stored pattern, the image analyzer 121 determines that the microfluidic device 200 has been normally loaded.

As described above, situations in which the microfluidic device 200 has not been normally loaded may include when the microfluidic device 200 has been loaded upside down, when a microfluidic device 200 has not been loaded at all, and when, although the microfluidic device 200 has been normally loaded, it does not have a pattern having the stored pattern characteristics.

As discussed above, the test apparatus 100 executes different operations in accordance with different configurations and arrangements of the microfluidic structure(s) formed on the microfluidic device 200. In this regard, when a microfluidic device that does not have a pattern having the stored pattern characteristics is loaded into the test apparatus 100, it may be determined as a microfluidic device that cannot be employed in the test apparatus 100.

Accordingly, when the characteristics of the detected pattern are different from those of the stored pattern, the image analyzer 121 determines that the microfluidic device 200 has not been normally loaded. Thus, it may be possible to eject the tray 150 not only when the microfluidic device 200 is loaded upside down, but also when a microfluidic device 200 is not loaded or when a microfluidic device unsuitable for the test apparatus 200 is loaded.

Concrete examples of pattern detection and determination of abnormal loading will be described in conjunction with an exemplary pattern region image illustrated in FIG. 6.

The image analyzer 121 first detects a pattern from the pattern region image Ip. For pattern detection, a general pattern detection algorithm may be applied. Based on a threshold value, an edge of the detected pattern may be extracted. Based on the extracted edge, a position of a comb tooth may be detected. A reference line of a lower end of the comb tooth may then be detected to calculate a height of the comb tooth from the reference line. Based on the calculated comb tooth height, the direction of the comb tooth may be normalized.

In the illustrated exemplary embodiment, the above-described pattern characteristics represent the direction of the comb tooth. The image analyzer 121 pre-stores the direction of the comb tooth corresponding to normal loading of the microfluidic device 200. In the exemplary embodiment of FIG. 6, the comb tooth direction corresponding to normal loading is inclined to the right. When the pattern region image transmitted from the optical sensor 110 is identical to the image illustrated in the right panel of FIG. 6, the image analyzer 121 determines that the comb tooth direction is inclined to the left. In this case, the determined comb pattern direction is different from that of the image corresponding to normal loading and, as such, the image analyzer 121 determines that the microfluidic device 200 has not been normally loaded.

On the other hand, when the pattern region image transmitted from the optical sensor 110 is identical to the image illustrated in the left panel of FIG. 6, the image analyzer 121 determines that the comb tooth direction is inclined to the right. In this case, the determined comb pattern direction is identical to that of the image corresponding to normal loading and, as such, the image analyzer 121 determines that the microfluidic device 200 has been normally loaded.

Of course, there is no limitation as to the kind of the pattern formed on the microfluidic device 200. Thus, any pattern may be suitable for the pattern P of the microfluidic device 200, so long as the pattern has a shape such that, when the pattern is reversed, the reversed pattern is vertically or laterally opposite to the normal pattern, or the pattern has a vertically or laterally asymmetrical shape.

Figure 7A:
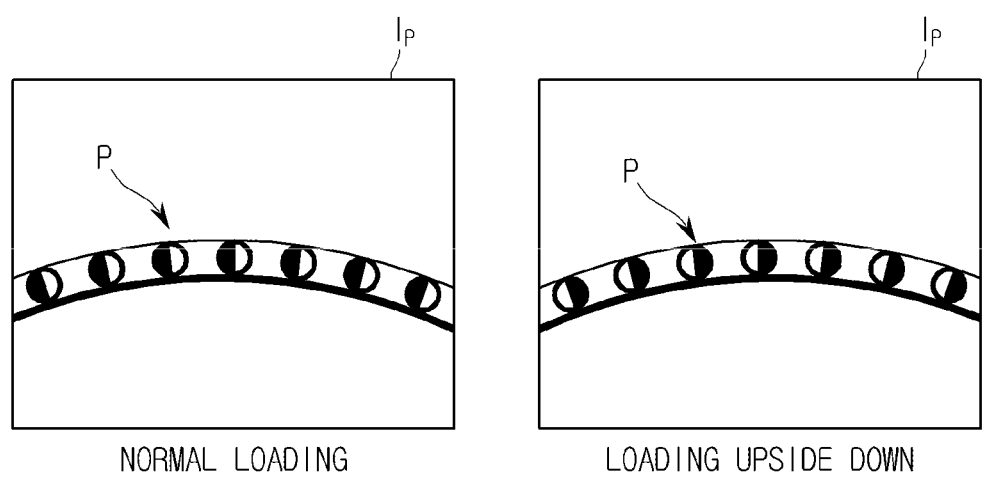
FIGS. 7A to 7C are views illustrating examples of patterns in accordance with various exemplary embodiments.
Figure 7B:
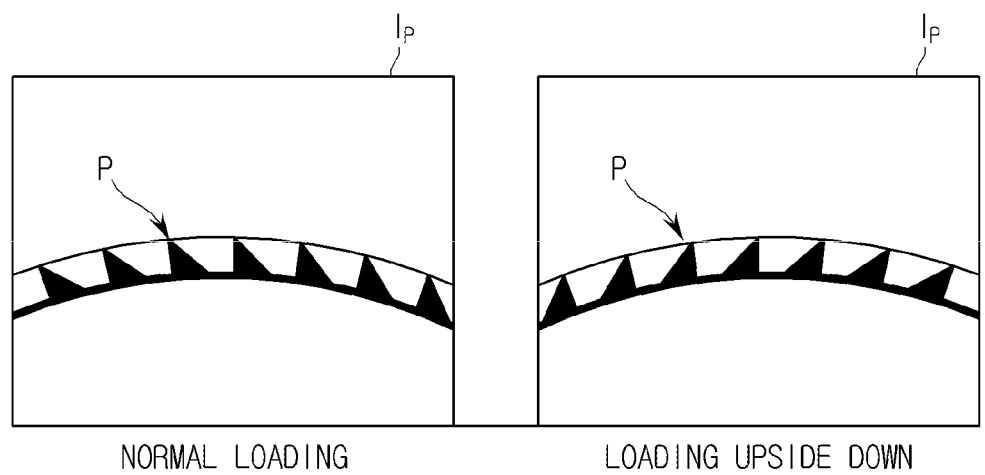
Figure 7C:
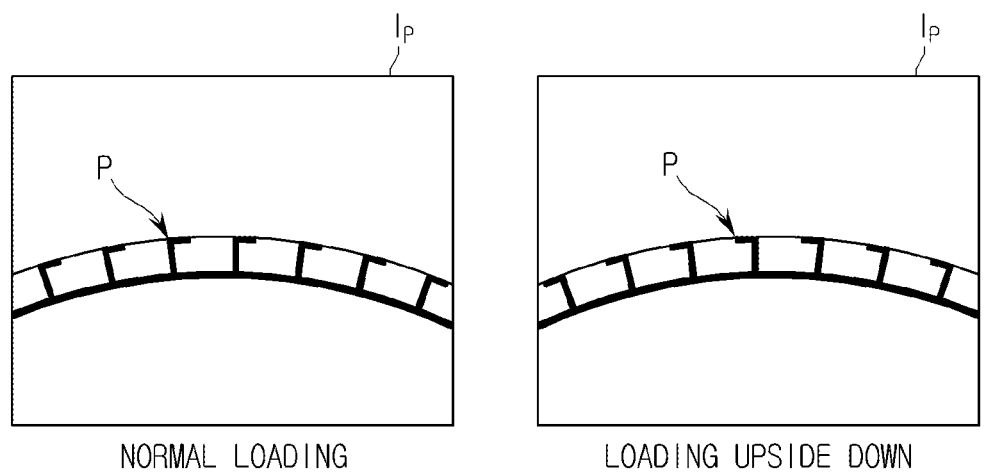

FIGS. 7A to 7C are views illustrating additional examples of patterns which may be formed on the microfluidic device.

As illustrated in FIG. 7A, the pattern may include pattern elements having different brightness values at left and right sides thereof. Thus, when the pattern is reversed, the brightness values of the pattern elements of the reversed pattern are opposite to those of the normal pattern.

Alternatively, as shown in FIG. 7B, one of the lines constituting each pattern element may have a predetermined inclination such that, when the pattern is reversed, the direction of the inclination of the line in the reversed pattern may be opposite to that of the normal pattern.

In addition, as shown in FIG. 7C, the pattern may have a laterally asymmetrical character shape.

The pattern may be formed on the circumference of the platform 210. That is, the pattern may include pattern elements repeatedly arranged in a circumferential direction of the platform 210. Of course, the pattern may be formed at only a portion of the circumference of the platform 210. In the former case, the pattern may have a laterally asymmetrical shape. On the other hand, in the latter case, the pattern may have a vertically asymmetrical shape.

When the pattern is formed at a portion of the circumference of the platform 210, detection of the pattern region is first carried out upon insertion of the tray 150 by controlling rotation of the microfluidic device 200 such that the pattern region is moved to a position corresponding to the optical sensor 110. For example, the microfluidic device 200 may be provided with a magnetic body at a position adjacent to the pattern region, and a magnet may be provided at a position adjacent to the optical sensor 110, to attract the magnetic body. Thus, the microfluidic device 200 may be moved in a circumferential direction, namely, rotated, to position the pattern region at a position facing the optical sensor 110 through attractive force between the magnetic body and the magnet.

When the pattern is formed surrounding the circumference of the platform 210, it may be possible to photograph the pattern region at any position on the circumference of the platform 210. In this case, the optical sensor 110 may directly photograph the pattern region without a separate operation to detect the pattern region. Thus, it may be possible to rapidly cope with abnormal loading.

Figure 8A:
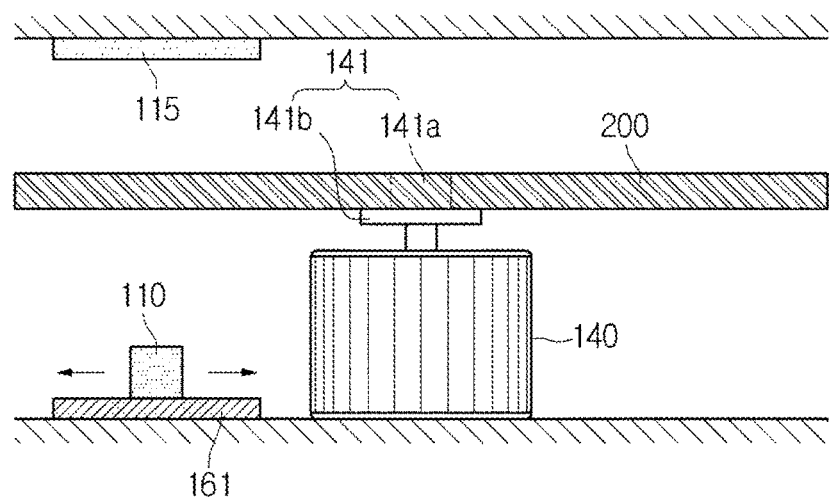
FIG. 8A is a side view illustrating an inner configuration of the test apparatus according to an exemplary embodiment.
Figure 8B:
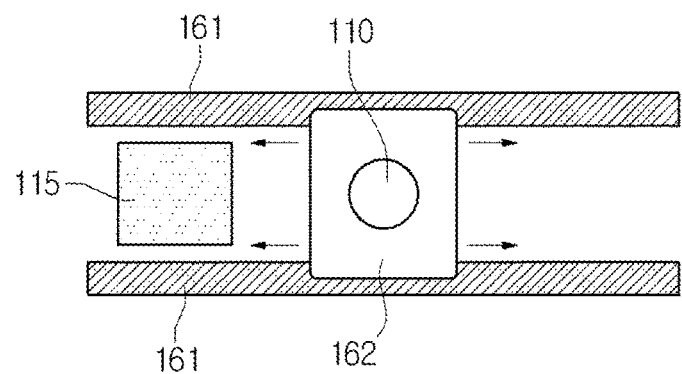
FIG. 8B is a plan view illustrating the inner configuration of the test apparatus according to the illustrated exemplary embodiment.

FIG. 8A is a side view illustrating an inner configuration of the test apparatus according to an exemplary embodiment. FIG. 8B is a plan view illustrating the inner configuration of the test apparatus according to the illustrated exemplary embodiment. FIG. 8B illustrates a region including a light emitter 115 in addition to the optical sensor 110.

Referring to FIGS. 8A and 8B, the test apparatus 100 may further include the light emitter 115, which irradiates light since the interior of the test apparatus 100 is dark. The optical sensor 110 senses light passing through the microfluidic device 200 or light reflected from the microfluidic device 200 and may photograph an image of the microfluidic device 200.

The light emitter 115 may include a surface light source having a large light emission area while being capable of uniformly emitting light, in order to irradiate light over a predetermined region of the microfluidic device 200. For example, a backlight unit or a light emitting diode (LED) may be employed as the light emitter 115.

As shown in FIG. 8A, the light emitter 115 may be mounted at a position facing the optical sensor 110 and, as such, the optical sensor 110 may sense light passing through the microfluidic device 200. As shown in FIG. 8B, the light emitter 115 may be mounted in parallel with the optical sensor 110 and, as such, the optical sensor 110 may sense light reflected from the microfluidic device 200.

As an example in which the light emitter 115 and optical sensor 110 are mounted in parallel, as shown in FIG. 8B, the light emitter 115 is mounted between two guide rails 161 to guide movement of a plate 162, on which the optical sensor 110 is mounted. In this case, the light emitter 115 emits light toward the microfluidic device 200 in parallel with the optical sensor 110.

The test apparatus 100 may be configured to compensate for errors generated due to various factors during detection of the pattern. Hereinafter, this will be described in detail.

Figure 9:
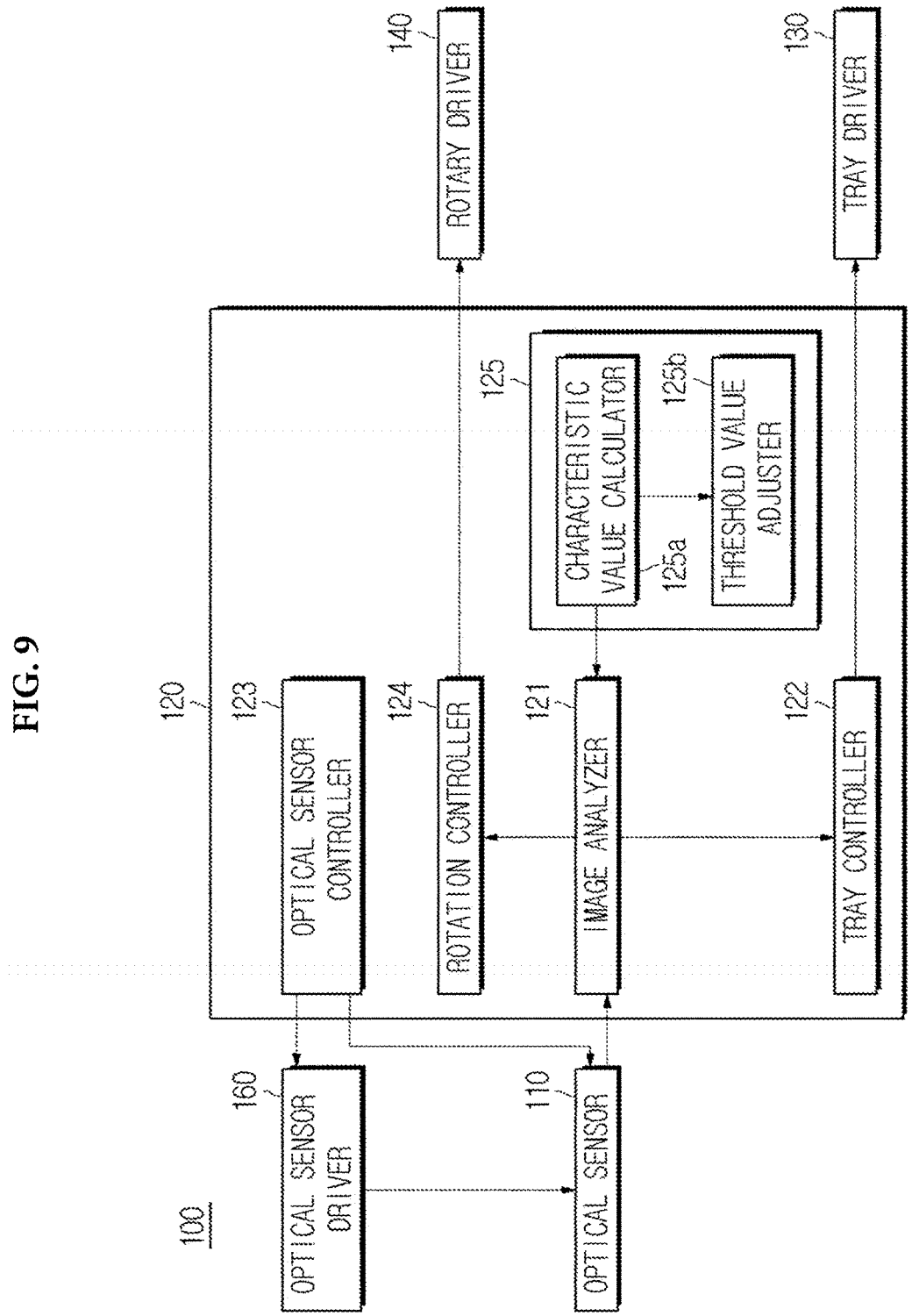
FIG. 9 is a block diagram illustrating a control configuration of the test apparatus for compensation for pattern detection errors in accordance with an exemplary embodiment.

FIG. 9 is a block diagram illustrating a control configuration of the test apparatus for compensation for pattern detection errors in accordance with an exemplary embodiment.

Referring to FIG. 9, the controller 120 may further include a compensator 125 configured to compensate for a pattern detection error, namely, a difference between a characteristic value of a pattern exhibited in a pattern region image and a reference characteristic value applied for pattern detection.

The optical characteristics of the pattern formed on the surface of the microfluidic device 200 may be varied in accordance with different manufacturers or different manufacture environments. In addition, as illustrated in FIG. 5, microfluidic structures such as channels or chambers may be overlapped with the pattern P. Furthermore, the transparency of the platform 210 in a region where the pattern P is disposed may be varied in accordance with different products. In each case, the characteristic value of the pattern exhibited in the pattern region image, for example, the brightness value of the pattern, may vary.

The following exemplary description will be given in conjunction with an example in which the pattern P is expressed by a grayscale. When a reference brightness value of 10 is stored as the brightness value of the pattern P formed on the microfluidic device 200, and the brightness value of the pattern exhibited in the pattern region image is 20, the pattern may be recognized by the image analyzer 121 as background when the threshold value of the reference brightness value is 15. In such cases, the threshold value applied in the image analyzer 121 may be adjusted in order to recognize the pattern.

Accordingly, it may be possible to compensate for pattern detection errors by adjusting the threshold value, based on the brightness value of the pattern exhibited in the pattern region image.

In particular, the compensator 125 may include a characteristic value calculator 125a to calculate the characteristic value of the pattern exhibited in the pattern region image, and a threshold value adjuster 125b to adjust the threshold value to be applied for pattern detection, based on the calculated characteristic value.

The characteristic value calculated in the characteristic value calculator 125a may be a brightness value. The characteristic value calculator 125a detects a reference pattern element from a plurality of pattern elements in the pattern region image. Thereafter, the characteristic value calculator 125a calculates a representative brightness value of the detected reference pattern element. The reference pattern element may be a pattern element which is easily distinguishable from a background, even when there is an error in the brightness value of the pattern. For example, as illustrated in FIG. 6, the reference line which is connected to a plurality of bars while having a long length, as compared to the bars, may be the reference pattern element.

The representative brightness value of the reference pattern element may be an average brightness value. The average brightness value may be an average of the brightness values of a plurality of regions in the reference pattern element. The brightness values of the plurality of regions may be a plurality of pixel values.

The threshold value adjuster 125b may therefore adjust a threshold value based on the calculated representative brightness value of the reference pattern element. For example, when the representative brightness value of the reference pattern element is higher than the reference brightness value applied for pattern detection, the threshold value is increased in accordance with the representative brightness value of the reference pattern element. In this case, the threshold value increase may be proportional to the representative brightness value of the reference pattern element or a difference between the representative brightness value of the reference pattern element and the reference brightness value.

Meanwhile, the threshold value may have an upper limit and a lower limit in accordance with the kind of the pattern. In this case, the upper limit or lower limit of the threshold value or both the upper and lower limits may be adjusted in accordance with whether the characteristic value of the reference pattern element is higher or lower than the reference characteristic value.

Figure 10:
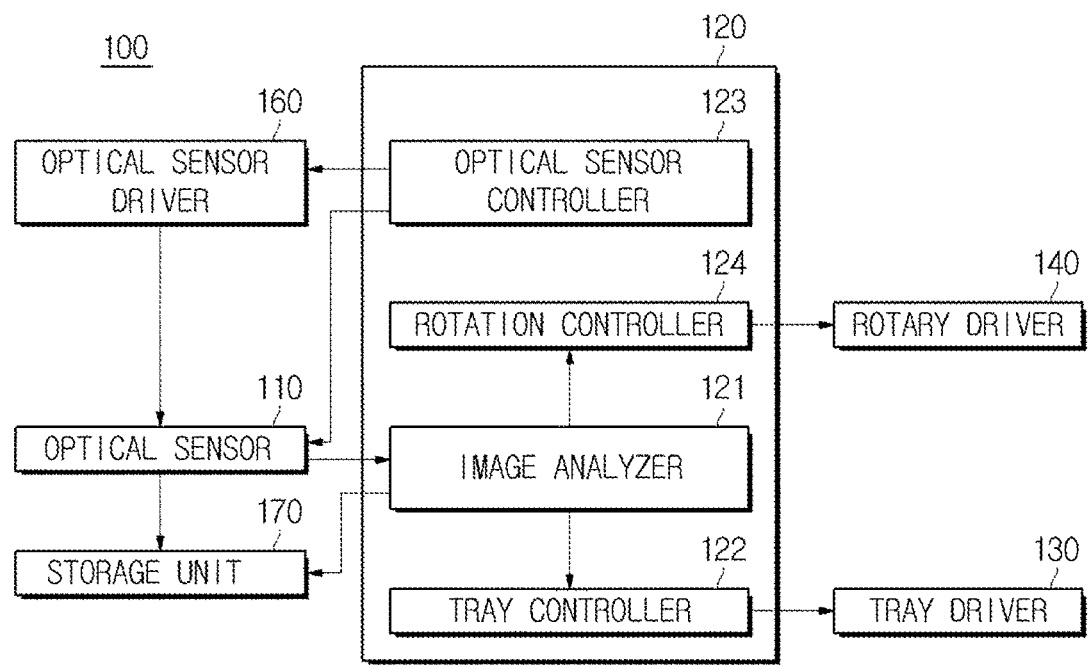
FIG. 10 is a block diagram illustrating the control configuration of the test apparatus which further includes a storage unit in accordance with an exemplary embodiment.

FIG. 10 is a block diagram illustrating the control configuration of the test apparatus which further includes a storage unit in accordance with an exemplary embodiment.

Referring to FIG. 10, the test apparatus 100 may further include a storage unit 170 to store a pattern region image photographed by the optical sensor 110 and/or results of a determination as to whether the microfluidic device 200 has been normally loaded. The storage unit 170 may include a memory such as a random access memory (RAM).

As described above, when a microfluidic device 200 is loaded into the test apparatus 100 upside down, a failure may occur. When the image analyzer 121 determines that the microfluidic device 200 has been abnormally loaded, the results of the determination and/or the photographed pattern region image is stored in the storage unit 170. Thus, when a service engineer is called to repair a failure, the engineer may easily determine the cause of the failure by reviewing information stored in the storage unit 170.

Depending on the storage capacity of the storage unit 170, it may be possible to store all the photographed pattern region images, irrespective of the results of the determination of the image analyzer 121. However, it may be possible to more efficiently manage the storage capacity of the storage unit 170 by storing the results of the determination and/or the photographed pattern region image only when the microfluidic device 200 has not been normally loaded.

Although not illustrated in the block diagram of FIG. 10, the above-described compensator 125 may also be included in the test apparatus 100 in addition to the storage unit 170.

Figure 11:
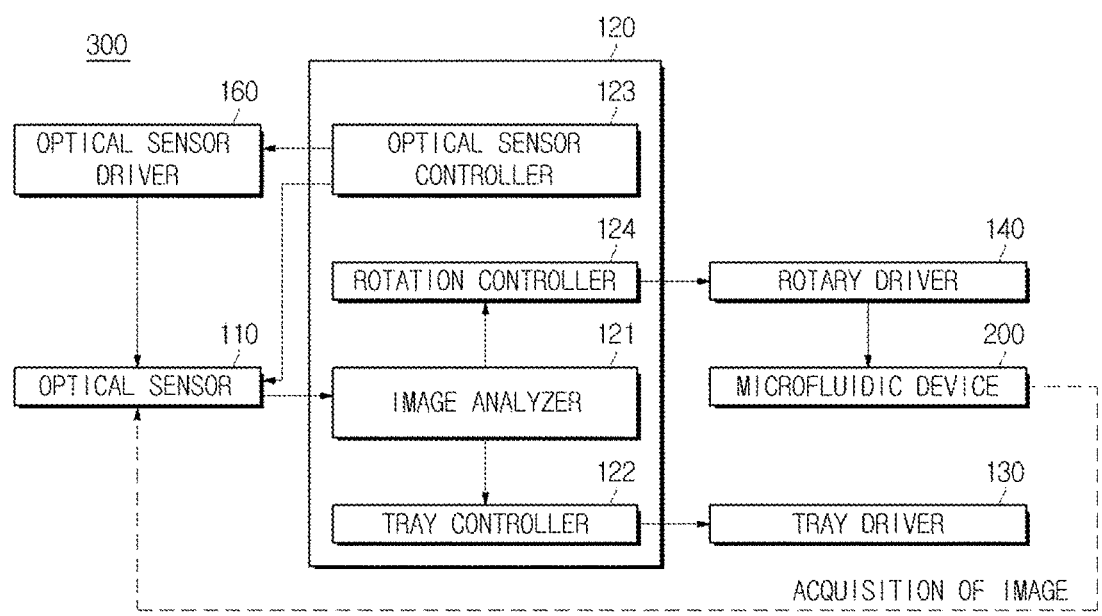
FIG. 11 is a block diagram illustrating a control configuration of a test system according to an exemplary embodiment.

FIG. 11 is a block diagram illustrating a control configuration of a test system according to an exemplary embodiment.

Referring to FIG. 11, the test system which is designated by reference numeral "300" includes a test apparatus 100, and a microfluidic device 200 to be loaded in the test apparatus 100.

The constituent elements of the test apparatus 100, namely, the optical sensor 110, controller 120, tray driver 130, rotary driver 140, and optical sensor driver 160, are identical to those of the above-described test apparatus 100 and, as such, no description thereof will be given. In addition, the above descriptions given of the test apparatus 100 and microfluidic device 200 may be applied to the test system 300.

Although not illustrated in the block diagram of FIG. 11, the test apparatus 100 which is included in the test system 300 may include the above-described compensator 125 and/or storage unit 170.

Hereinafter, a control method for the test apparatus according to an exemplary embodiment will be described. The above-described test apparatus 100 may be applied to the control method for the test apparatus according to the illustrated exemplary embodiment.

Figure 12:
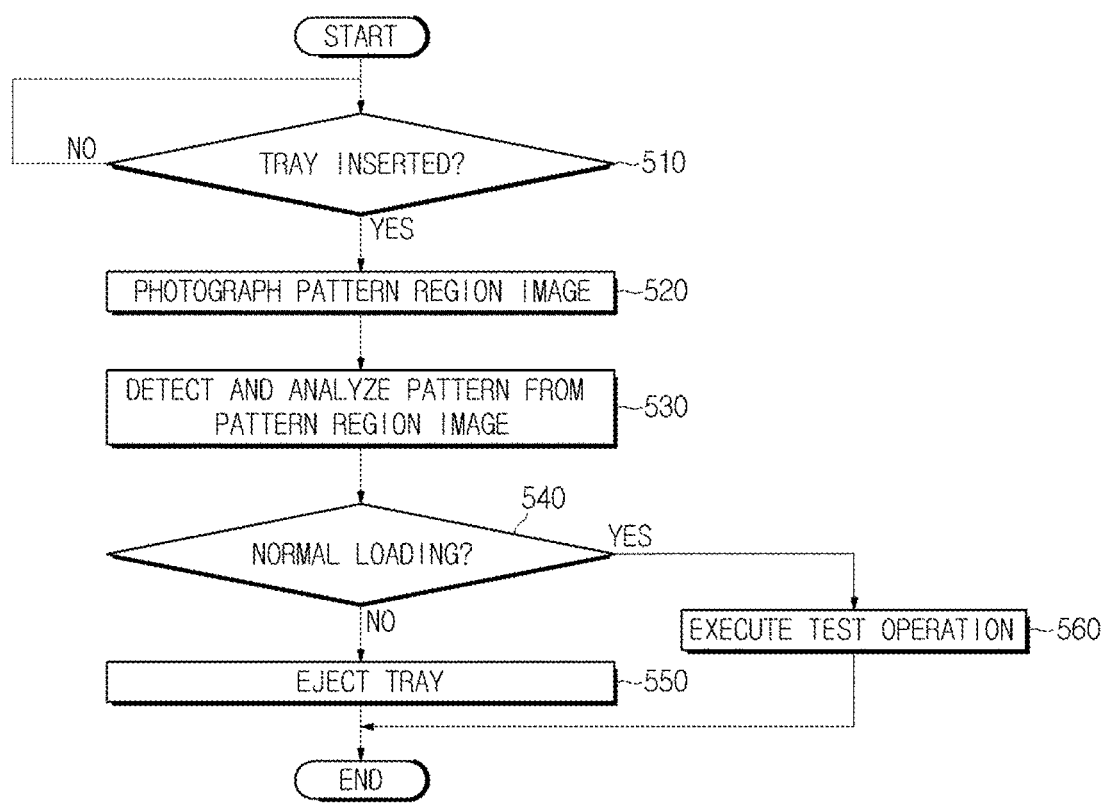
FIG. 12 is a flowchart illustrating a control method for the test apparatus according to an exemplary embodiment.

FIG. 12 is a flowchart illustrating a control method for the test apparatus according to an exemplary embodiment.

Referring to FIG. 12, it is determined whether the tray has been loaded (510). When the tray has been loaded ("YES"

in operation 510), a pattern region image is photographed using the optical sensor 110. As discussed above, the "pattern region image" means an image photographed at a position corresponding to the microfluidic device 200, and more particularly, to an image photographed at a position corresponding to a pattern region.

The position corresponding to the pattern region of the microfluidic device 200 may be predetermined. When the optical sensor 110 is disposed beneath the microfluidic device 200, the optical sensor 110 may be positioned at a position misaligned with the inlet 221 or a position that does not face the inlet 221 in order to prevent the optical sensor 110 from being contaminated by any sample leaking through the inlet 221 if the microfluidic device 200 was loaded upside down.

Thereafter, a pattern is detected from the pattern region image, and the detected pattern is analyzed (530). Detection and analysis of the pattern may be executed using one of various pattern detection algorithms. When a pattern is detected, the detected pattern is analyzed to determine the characteristics of the pattern.

It is then determined whether the microfluidic device has been normally loaded (540). For this determination, it is determined whether the characteristics of the pattern are identical to the pre-stored pattern characteristics, namely, the pattern characteristics corresponding to normal loading. When the characteristics of the pattern are different from the pre-stored pattern characteristics, it is determined that normal loading has not been achieved. On the other hand, when the characteristics of the pattern are identical to the pre-stored pattern characteristics, it is determined that normal loading has been achieved.

Here, the case in which normal loading has not been achieved may include the case in which the microfluidic device has been abnormally loaded, and the case in which the microfluidic device has not been loaded. In addition, the case in which the microfluidic device has been abnormally loaded may include the case in which the microfluidic device has been loaded in a reversed state, and the case in which the microfluidic device 200 does not have a pattern having the stored pattern characteristics.

Upon determining that the microfluidic device has not been normally loaded ("NO" in operation 540), the tray is ejected (550), to minimize contamination of the test apparatus 100 caused by abnormal loading of the microfluidic device.

Upon determining that the microfluidic device has been normally loaded ("YES" in operation 540), a test operation of the test apparatus 100 is executed (560). Execution of the test operation may be achieved by repeating rotation and stopping of the microfluidic device in accordance with a sequence suitable for the microfluidic device 200.

Figure 13:
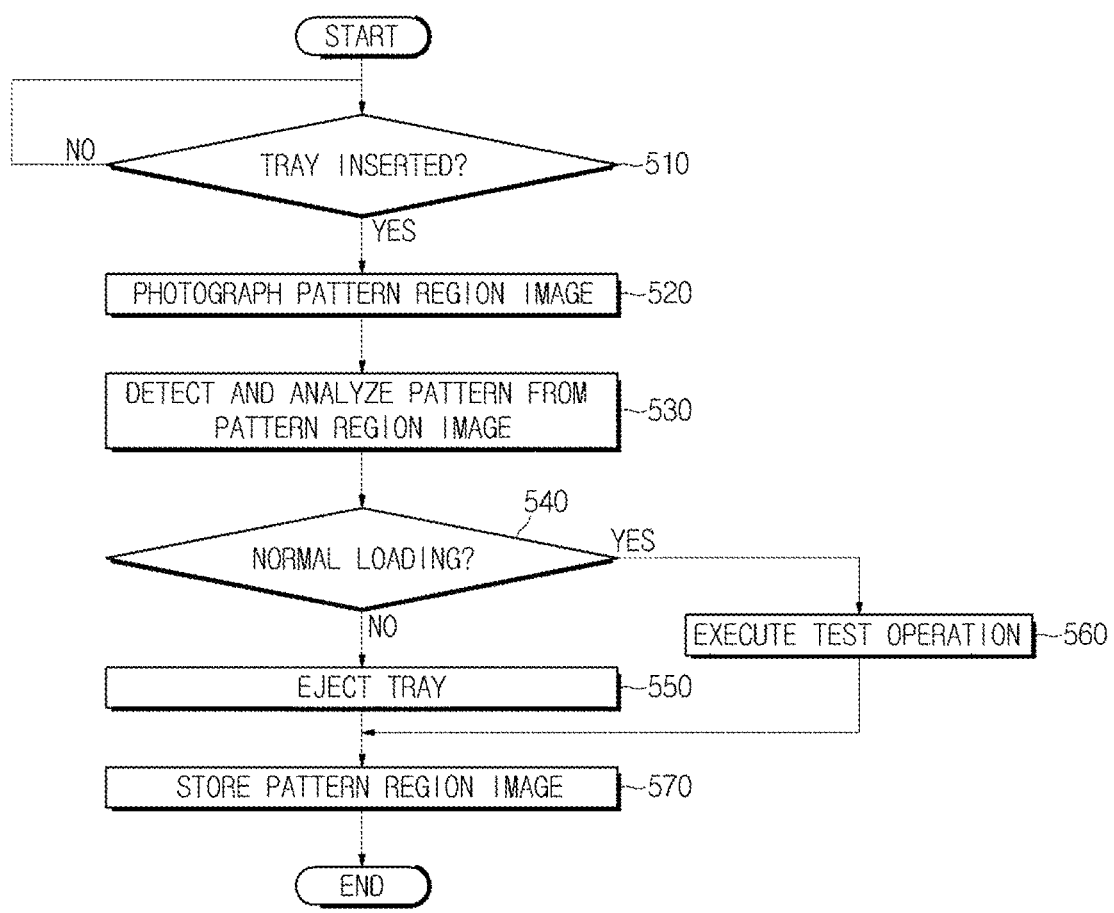
FIG. 13 is a flowchart illustrating a control method for the test apparatus according to an exemplary embodiment, in which a pattern region image may be stored.

FIG. 13 is a flowchart illustrating a control method for the test apparatus according to an exemplary embodiment in which a pattern region image may be stored.

Referring to FIG. 13, the procedure from operation 510 of determining whether the tray has been inserted to operation 550 of ejecting the tray or operation 560 of executing a test operation in accordance with whether the microfluidic device has been normally loaded is identical to that of FIG. 12.

Upon determining that the microfluidic device has not been normally loaded ("NO" in operation 540), the tray is immediately ejected (550). Subsequently, the pattern region image is stored in the memory (570). Alternatively, or in addition thereto, results of determination as to whether normal loading has been achieved may be stored. As discussed above, when the microfluidic device 200 is loaded upside down, a failure may occur. To this end, upon determining that the microfluidic device 200 has not been normally loaded, results of the determination and/or the photographed pattern region image is stored in the memory. In this case, when a service engineer performs after-service to repair a failure, the cause of such failure may be easily determined by identifying information stored in the memory.

Depending on the storage capacity of the memory, it may be possible to store all the photographed pattern region images, irrespective of the results of the determination as to whether normal loading has been achieved. However, it may be possible to more efficiently manage the storage capacity of the memory by storing the results of the determination and/or the photographed pattern region image only when the microfluidic device 200 has not been normally loaded.

Figure 14:
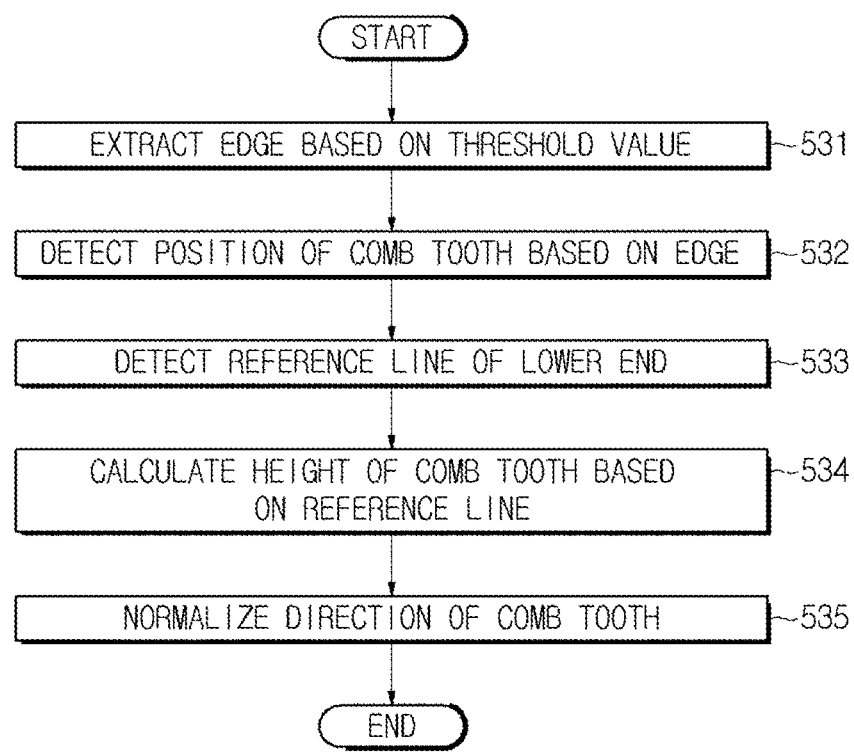
FIG. 14 is a flowchart illustrating an example of the procedure of detecting and analyzing a pattern in the control method for the test apparatus according to an exemplary embodiment.

FIG. 14 is a flowchart illustrating an example of the procedure of detecting and analyzing a pattern in the control method for the test apparatus according to an exemplary embodiment.

As discussed above the pattern formed on the microfluidic device 200 may have a shape such that, when the pattern is reversed, the reversed pattern is vertically or laterally opposite to the normal pattern. That is, the pattern has a vertically or laterally asymmetrical shape. Accordingly, when the microfluidic device 200 is loaded upside down, the direction of the pattern is reversed and, as such, it may be possible to determine abnormal loading of the microfluidic device 200.

For example, a pattern having a comb tooth shape as shown in FIG. 3A may be formed on the microfluidic device 200. In this case, the optical sensor 110 may photograph a pattern region image Ip as shown in FIG. 6.

In the case in which the comb tooth pattern is formed on the microfluidic device 200, an edge is extracted from the pattern region image, based on a threshold value (531). Based on the extracted edge, a position of a comb tooth is detected (532).

In addition, a reference line of a lower end of the comb tooth is detected (533), and the height of the comb tooth is calculated, based on the detected reference line (534). Based on the calculated height, the direction of the comb tooth is normalized (535).

Again referring to FIG. 12, the procedure of FIG. 14 may be executed in order to detect and analyze a pattern from the pattern region image (530). Since the comb tooth direction corresponding to normal loading of the microfluidic device 200 is stored, it may be possible to compare the normalized comb tooth direction with the stored comb tooth direction for determination as to normal loading (540). When the normalized comb tooth direction is identical to the stored comb tooth direction, it is determined that the microfluidic device 200 has been normally loaded. In this case, a test operation is executed (560). On the other hand, when the normalized comb tooth direction is different from the stored comb tooth direction, it is determined that the microfluidic device 200 has been abnormally loaded or has not been loaded. In this case, the tray is ejected (550).

Of course, the procedure of detecting and analyzing the pattern may vary in accordance with the shape of the pattern formed on the microfluidic device 200. The procedure of FIG. 14 is only an example applied to the case in which the pattern formed on the microfluidic device 200 has a comb tooth shape.

Figure 15:
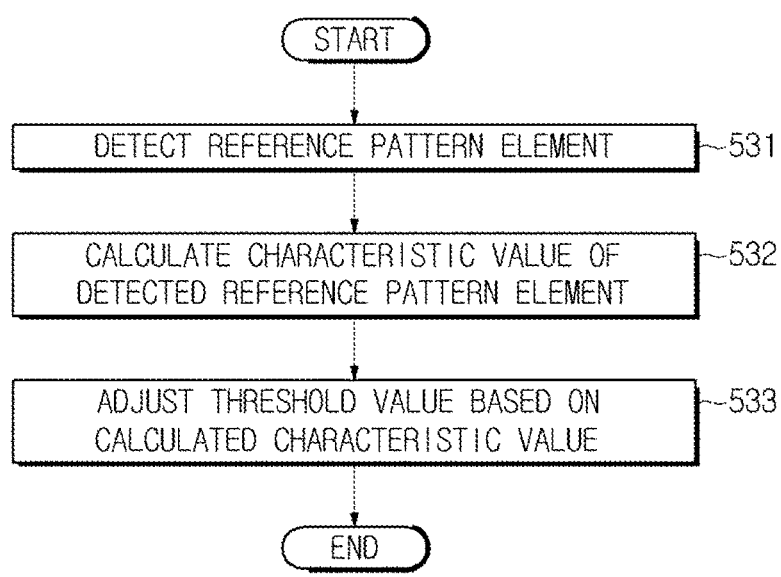
FIG. 15 is a flowchart illustrating a procedure of compensating for errors caused by various factors during pattern detection in the control method for the test apparatus according to an exemplary embodiment.

FIG. 15 is a flowchart illustrating a procedure of compensating for errors caused by various factors during pattern detection in the control method for the test apparatus according to an exemplary embodiment.

The optical characteristics of the pattern formed on the surface of the microfluidic device 200 may vary in accordance with different manufacturers or different manufacture environments. In addition, as illustrated in FIG. 5, microfluidic structures such as channels 251 or chambers 253 may be overlapped with the pattern. Furthermore, the transparency of the platform 210 in a region where the pattern is disposed may vary in accordance with different products. In these cases, the characteristic value of the pattern exhibited in the pattern region image, for example, the brightness value of the pattern, may vary.

In the control method for the test apparatus according to the illustrated exemplary embodiment, the characteristic value of the pattern exhibited in the pattern region image is first calculated in order to compensate for errors caused by the above-described variations. In an example of calculation of the characteristic value of the pattern, a reference pattern element is detected from the pattern region image (531), and the characteristic value of the detected reference pattern element is calculated (532).

The reference pattern element is a pattern element which is easily distinguishable from a background, even when there is an error in the brightness value of the pattern. For example, as illustrated in FIG. 6, the reference line which is connected to a plurality of bars while having a long length, as compared to the bars, may be the reference pattern element.

The characteristic value of the reference pattern element may be a representative brightness value of the reference pattern element. The representative brightness value may be an average brightness value. The average brightness value may be an average of the brightness values of a plurality of regions in the reference pattern element. The brightness values of the plural regions may be a plurality of pixel values.

A threshold value may be adjusted based on the calculated characteristic value (533). The threshold value is applied for pattern detection. As described in conjunction with FIG. 14, an edge of the pattern is extracted, based on the threshold value.

When the representative brightness value of the reference pattern element is higher than the reference brightness value applied for pattern detection, the threshold value is increased in accordance with the representative brightness value of the reference pattern element. In this case, the threshold value increase may be proportional to the representative brightness value of the reference pattern element or a difference between the representative brightness value of the reference pattern element and the reference brightness value.

In accordance with the above-described test apparatus 100, microfluidic device 200, test system 300, and control method for the test apparatus 100, it may be possible to immediately unload the microfluidic device 200 when the microfluidic device 200 is abnormally loaded in the test apparatus 100, thereby minimizing contamination of the test apparatus 100 by the sample.

As apparent from the above description, in the microfluidic device, the test apparatus, the test system including the same, and the control method for the test apparatus, it may be possible to rapidly detect abnormal loading of the microfluidic device, and to unload the abnormally-loaded microfluidic device, thereby preventing contamination of the test apparatus by a sample and degradation in reliability of test results.

Although a few exemplary embodiments have been shown and described, it would be appreciated by those skilled in the art that changes may be made in these embodiments without departing from the principles and spirit of the inventive concept, the scope of which is defined in the claims and their equivalents.

What is claimed is:

1. A system for testing a sample received in a microfluidic device, comprising:
   the microfluidic device; and
   a test apparatus including:
   an optical sensor configured to photograph an image at a position corresponding to the microfluidic device; and
   a controller configured to detect a pattern formed on a surface of the microfluidic device based on the photographed image, and to determine whether characteristics of the detected pattern are identical to characteristics of a pre-stored pattern, and to determine that the microfluidic device has not been normally loaded in the test apparatus, when the characteristics of the detected pattern are different from the characteristics of the pre-stored pattern;
   wherein when the microfluidic device has been normally loaded in the test apparatus, an inlet formed at the microfluidic device for injection of the sample is facing upward; and
   wherein when the microfluidic device has been loaded in the test apparatus, but has not been normally loaded in the test apparatus, the controller is configured to cause ejection of the microfluidic device from the test apparatus,
   wherein the controller is configured to determine that the microfluidic device has not been normally loaded when the microfluidic device has been loaded upside down.

2. The system according to claim 1, wherein the controller is configured to pre-store a direction of a pattern corresponding to normal loading of the microfluidic device, to determine whether a vertical or lateral direction of the detected pattern is opposite to the pre-stored pattern direction, and to determine that the microfluidic device has not been normally loaded upon determining that the vertical or lateral direction of the detected pattern is opposite to the pre-stored pattern direction.

3. The system according to claim 1, further comprising a tray insertable into and ejectable from an interior of the test apparatus, wherein the tray carries the microfluidic device.

4. The system according to claim 3, wherein the controller is further configured to control the optical sensor to photograph an image at a position corresponding to the microfluidic device when the tray is inserted into the test apparatus.

5. The system according to claim 4, wherein the controller is configured to control the tray to be ejected from the test apparatus upon determining that the microfluidic device has not been normally loaded.

6. The system according to claim 4, wherein the optical sensor is movable in a radial direction of the microfluidic device.

7. The system according to claim 6, wherein the position corresponding to the microfluidic device is a position that corresponds to a pattern region including the pattern.

8. The system according to claim 7, wherein the controller is further configured to control the optical sensor to photograph the image at a position that does not correspond to an inlet formed at the microfluidic device, for injection of the sample.

9. The system according to claim 7, wherein the controller is configured to position the optical sensor at an initial position corresponding to the microfluidic device.

10. The system according to claim 1, further comprising a storage unit configured to store one or more of the photographed image or results of determining that the microfluidic device has not been normally loaded.

11. The system according to claim 1, further comprising a light emitter mounted at a position facing the optical sensor or in parallel with the optical sensor.

12. A system for testing a sample received in a microfluidic device, comprising:
the microfluidic device; and
a test apparatus including:
an optical sensor configured to photograph an image at a position corresponding to the microfluidic device; and
a controller configured to detect a pattern formed on a surface of the microfluidic device based on the photographed image, and to determine whether characteristics of the detected pattern are identical to characteristics of a pre-stored pattern, and to determine that the microfluidic device has not been normally loaded in the test apparatus, when the characteristics of the detected pattern are different from the characteristics of the pre-stored pattern;
wherein when the microfluidic device has been normally loaded in the test apparatus, an inlet formed at the microfluidic device for injection of the sample is facing upward; and
wherein when the microfluidic device has been loaded in the test apparatus, but has not been normally loaded in the test apparatus, the controller is configured to cause ejection of the microfluidic device from the test apparatus,
wherein the pre-stored pattern is a pattern corresponding to normal loading of the microfluidic device,
wherein the controller is configured to compensate for a difference between a brightness value of a pattern exhibited in the photographed image and a reference brightness value applied for detection of the pattern,
wherein the pattern formed on the microfluidic device comprises a plurality of pattern elements; and
wherein the controller is configured to detect a reference element from among the plurality of pattern elements in the photographed image, and to adjust a threshold value corresponding to the reference brightness value based on a representative brightness value of the detected reference pattern element.

13. The system according to claim 12, wherein the controller is configured to pre-store a direction of a pattern corresponding to normal loading of the microfluidic device, to determine whether a vertical or lateral direction of the detected pattern is opposite to the pre-stored pattern direction, and to determine that the microfluidic device has not been normally loaded upon determining that the vertical or lateral direction of the detected pattern is opposite to the pre-stored pattern direction.

14. The system according to claim 12, further comprising a tray insertable into and ejectable from an interior of the test apparatus, wherein the tray carries the microfluidic device.

15. The system according to claim 14, wherein the controller is further configured to control the optical sensor to photograph an image at a position corresponding to the microfluidic device when the tray is inserted into the test apparatus.

16. The system according to claim 15, wherein the controller is configured to control the tray to be ejected from the test apparatus upon determining that the microfluidic device has not been normally loaded.

17. The system according to claim 15, wherein the optical sensor is movable in a radial direction of the microfluidic device.

18. The system according to claim 17, wherein the position corresponding to the microfluidic device is a position that corresponds to a pattern region including the pattern.

19. The system according to claim 18, wherein the controller is further configured to control the optical sensor to photograph the image at a position that does not correspond to an inlet formed at the microfluidic device, for injection of the sample.

20. The system according to claim 18, wherein the controller is configured to position the optical sensor at an initial position corresponding to the microfluidic device.

21. The system according to claim 12, further comprising a storage unit configured to store one or more of the photographed image or results of determining that the microfluidic device has not been normally loaded.

22. The system according to claim 12, further comprising a light emitter mounted at a position facing the optical sensor or in parallel with the optical sensor.

23. A system for testing a sample received in a microfluidic device, comprising:
the microfluidic device; and
a test apparatus including:
an optical sensor configured to photograph an image at a position corresponding to the microfluidic device; and
a controller configured to detect a pattern formed on a surface of the microfluidic device based on the photographed image, and to determine whether characteristics of the detected pattern are identical to characteristics of a pre-stored pattern, and to determine that the microfluidic device has not been normally loaded in the test apparatus, when the characteristics of the detected pattern are different from the characteristics of the pre-stored pattern;
wherein when the microfluidic device has been normally loaded in the test apparatus, an inlet formed at the microfluidic device for injection of the sample is facing upward;
wherein when the microfluidic device has been loaded in the test apparatus, but has not been normally loaded in the test apparatus, the controller is configured to cause ejection of the microfluidic device from the test apparatus, and
wherein the pattern has a vertically or laterally asymmetrical shape.

24. The system according to claim 23, wherein the controller is configured to pre-store a direction of a pattern corresponding to normal loading of the microfluidic device, to determine whether a vertical or lateral direction of the detected pattern is opposite to the pre-stored pattern direction, and to determine that the microfluidic device has not been normally loaded upon determining that the vertical or lateral direction of the detected pattern is opposite to the pre-stored pattern direction.

25. The system according to claim 23, further comprising a tray insertable into and ejectable from an interior of the test apparatus, wherein the tray carries the microfluidic device.

26. The system according to claim 25, wherein the controller is further configured to control the optical sensor to photograph an image at a position corresponding to the microfluidic device when the tray is inserted into the test apparatus.

27. The system according to claim 26, wherein the controller is configured to control the tray to be ejected from the test apparatus upon determining that the microfluidic device has not been normally loaded.

28. The system according to claim 26, wherein the optical sensor is movable in a radial direction of the microfluidic device.

29. The system according to claim 28, wherein the position corresponding to the microfluidic device is a position that corresponds to a pattern region including the pattern.

30. The system according to claim 29, wherein the controller is further configured to control the optical sensor to photograph the image at a position that does not correspond to an inlet formed at the microfluidic device, for injection of the sample.

31. The system according to claim 29, wherein the controller is configured to position the optical sensor at an initial position corresponding to the microfluidic device.

32. The system according to claim 23, further comprising a storage unit configured to store one or more of the photographed image or results of determining that the microfluidic device has not been normally loaded.

33. The system according to claim 23, further comprising a light emitter mounted at a position facing the optical sensor or in parallel with the optical sensor.

* * * * *